(12) United States Patent
Kaplan

(10) Patent No.: US 6,767,336 B1
(45) Date of Patent: Jul. 27, 2004

(54) AUTOMATIC INJECTOR

(76) Inventor: Sheldon Kaplan, 3199 Shoreline Dr., Clearwater, FL (US) 33760

( * ) Notice: Subject to any disclaimer, the term of this patent is extended or adjusted under 35 U.S.C. 154(b) by 6 days.

(21) Appl. No.: 10/248,328

(22) Filed: Jan. 9, 2003

(51) Int. Cl.[7] .............................................. A61M 5/20
(52) U.S. Cl. ..................................... 604/136; 604/131
(58) Field of Search ................................ 604/136, 135, 604/134, 208, 211, 131, 132, 133, 137, 138, 272, 274

(56) References Cited

U.S. PATENT DOCUMENTS

| | | | | |
|---|---|---|---|---|
| 3,797,489 A | * | 3/1974 | Sarnoff | 604/136 |
| 5,176,643 A | * | 1/1993 | Kramer et al. | 604/135 |
| 5,665,071 A | * | 9/1997 | Wyrick | 604/134 |

* cited by examiner

*Primary Examiner*—Manuel Mendez
(74) *Attorney, Agent, or Firm*—Ronald E. Smith; Smith & Hopen, P.A.

(57) ABSTRACT

A first embodiment of an automatic injector employs less material and fewer parts by eliminating an outer housing required in earlier automatic injectors. In a second embodiment, a manually operated sharps protector is provided. In a third embodiment, the sharps protector is deployed by a spring positioned internally of the sharps protector. In a fourth embodiment, the sharps protector is deployed by a spring positioned externally of the sharps protector. In all embodiments, removal of a safety cap enables a user to press on an outer gun sleeve that displaces in an axial direction and releases the trailing end of a spring holder so that a compressed spring that bears against the spring holder unloads and drives a piston that displaces a cannula into the tissue of a user, followed by a liquid medicament injection through the cannula.

28 Claims, 5 Drawing Sheets

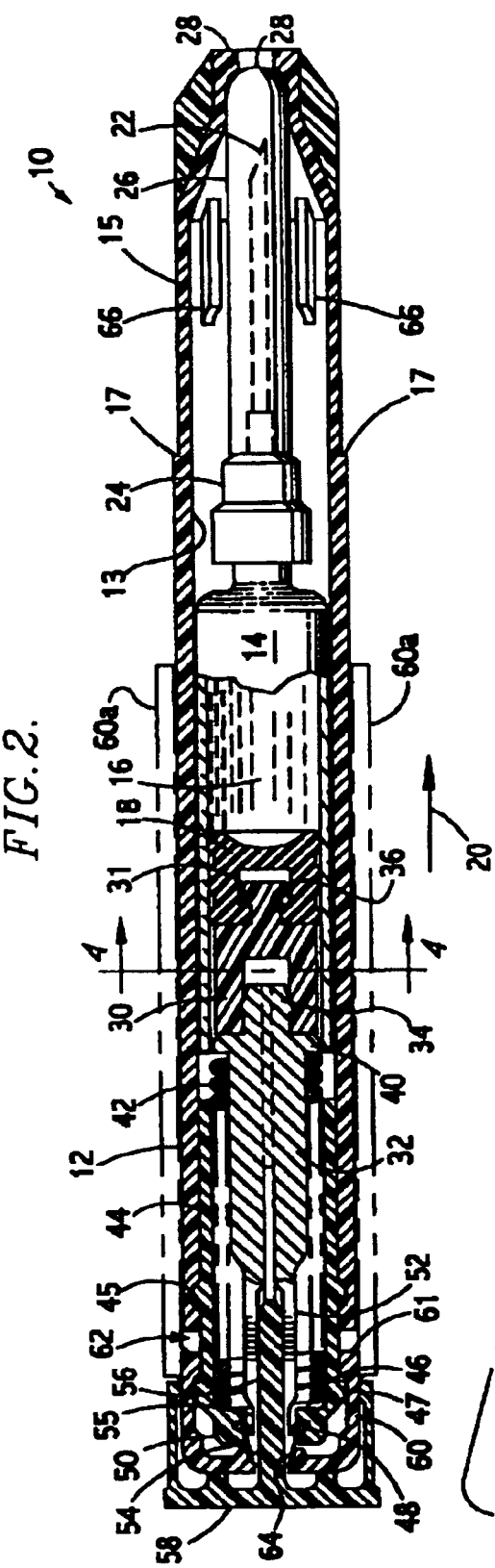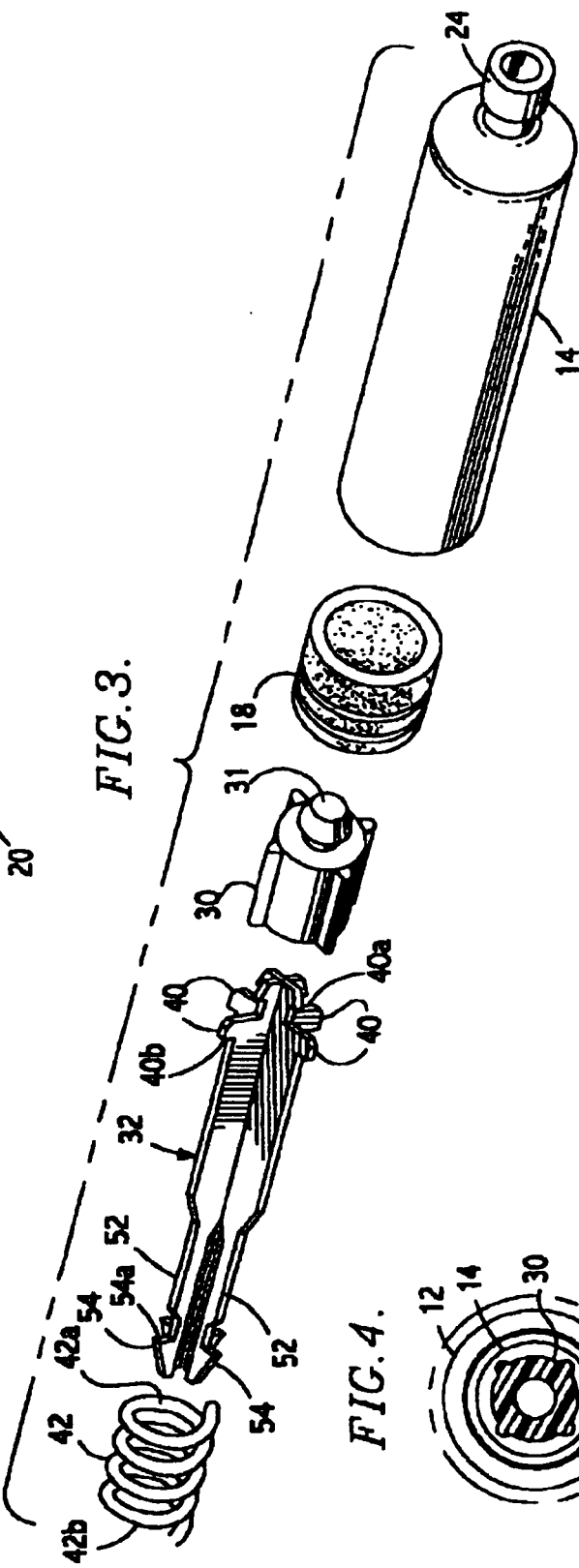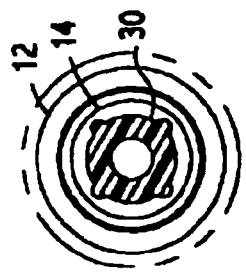

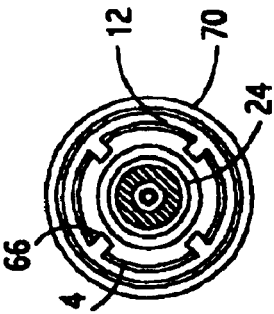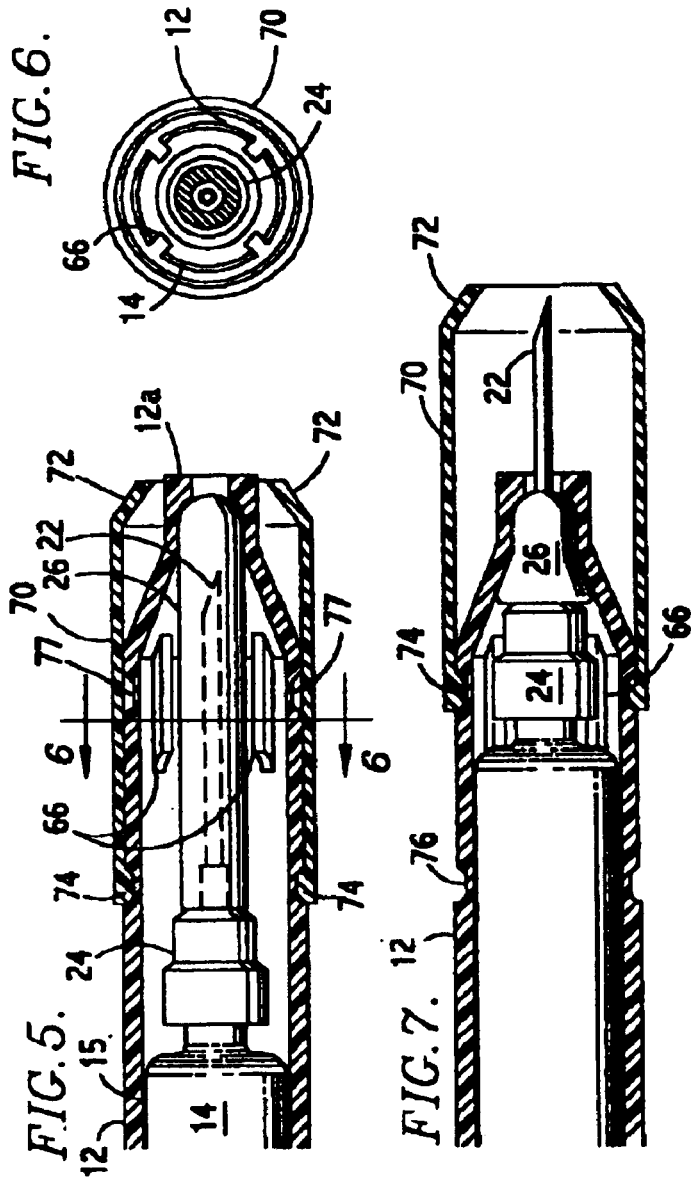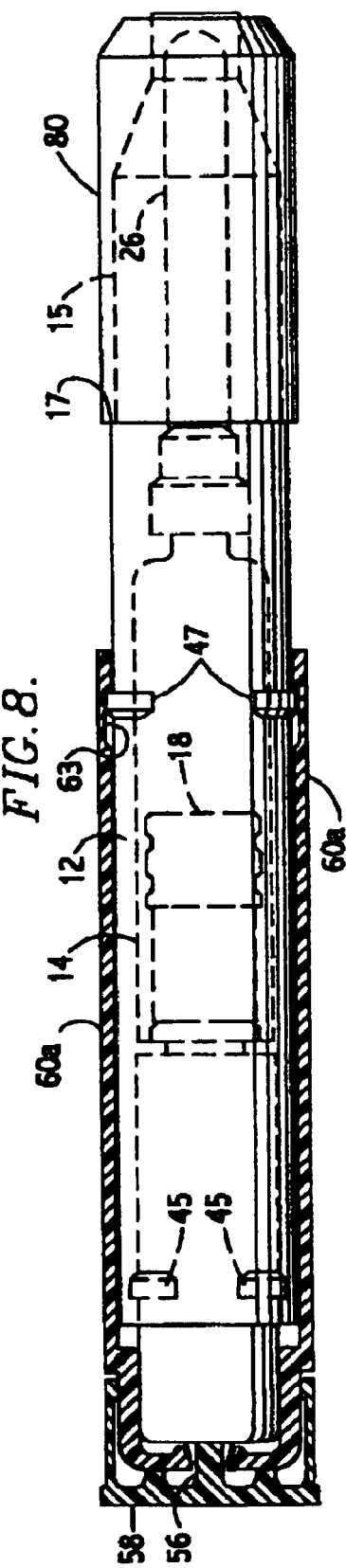

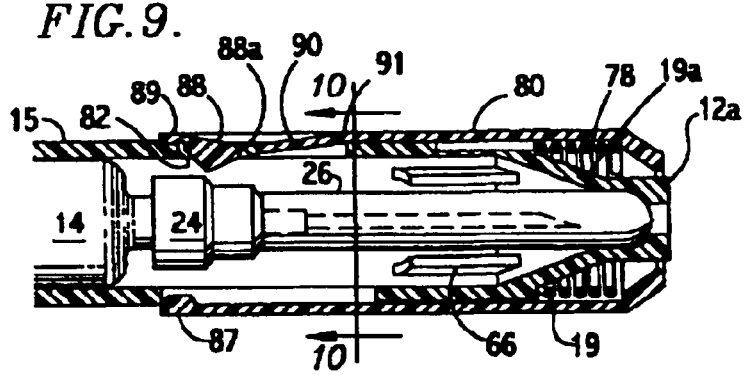
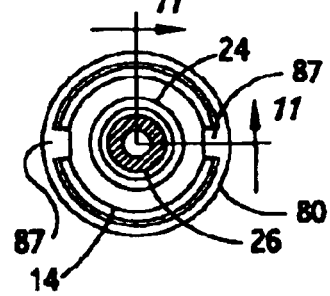
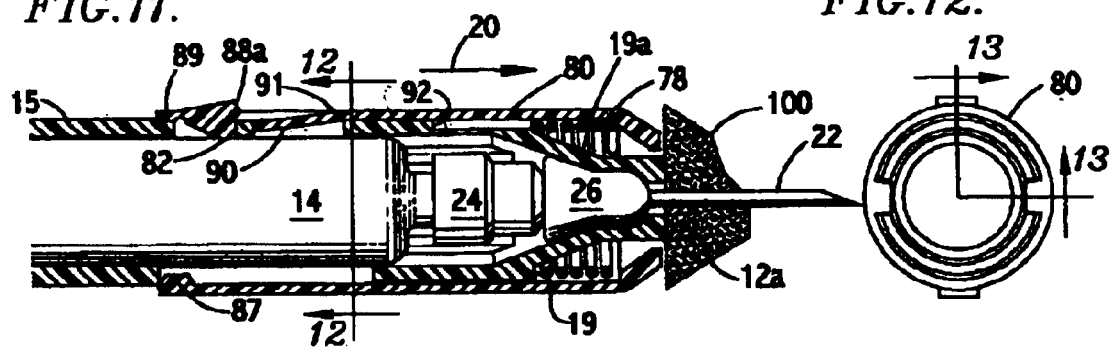
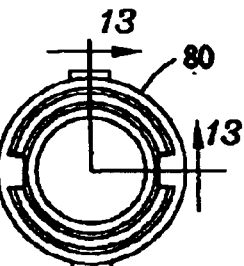
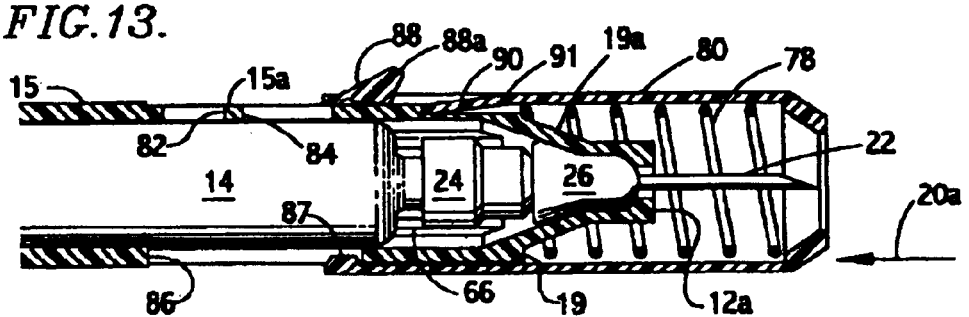
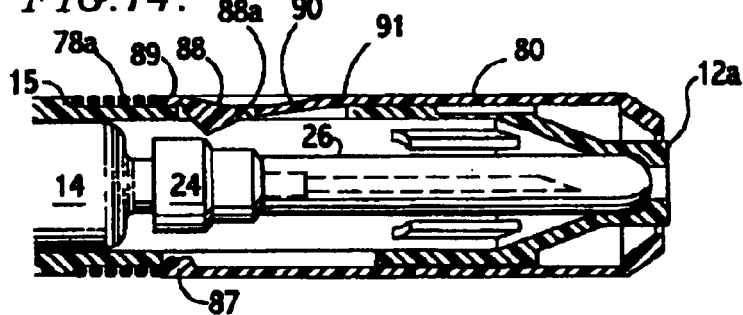

AUTOMATIC INJECTOR

BACKGROUND OF THE INVENTION

1. Field of the Invention

This invention relates to improvements in automatic injectors. Additional embodiments include a sharps protector that is manually or automatically operable.

2. Description of the Prior Art

Military personnel under chemical attack are trained to use automatic injectors when an injection is needed on an emergency basis in the field where medical personnel are not available to perform the injection. Civilians or military personnel who are allergic to bee or wasp stings, and the like, may use them when there is no access to emergency medical service (EMS) personnel or insufficient time to travel to a medical facility. Passenger aircraft are often equipped with automatic injectors as well for use when a passenger has a food allergy that creates a medical emergency. Most emergency medical vehicles also carry automatic injectors for the emergency treatment of allergic reactions. There are other uses for automatic injectors as well.

The automatic injector disclosed in expired U.S. Pat. No. 4,031,893, commercially known as the EpiPen® epinephrine auto-injector, invented primarily by the present inventor, has been in widespread use for more than twenty years. The military version thereof is known as the Pralidoxime ComboPen. The user grasps an outer cylindrical sleeve of the injector and delivers the leading end of the device to the injection site with a force sufficient to cause release of a spring-loaded needle. More specifically, when the device is ready to be used, the outer cylindrical sleeve trails an inner cylinder from which the needle or cannula extends so that when the leading end of the outer cylindrical sleeve hits the user's skin, the movement of the trailing end of the outer cylindrical sleeve releases a spring and the spring drives a piston that pushes liquid medicament out of a cartridge and Into the user's tissue through the cannula.

The '893 device fulfilled the needs of its (pre-AIDS) time, but it includes no means for covering the sharp cannula after it has been deployed. Thus, the exposed cannula represents a hazard to those who come into contact with it after it has been withdrawn from the tissue of the user. Nor is it a simple matter to retrofit the cannula with a sharps protector because there is insufficient space within which to mount a sharps protector.

The '893 device also uses a relatively large amount of plastic material in its construction due to the aforesaid outer cylindrical sleeve.

Another drawback of the '893 device is that the user must aim at and hit the desired point of injection in one motion. Impact of the device against the user's body triggers extension of the cannula by causing the release of a loaded piston biasing means if the device works in accordance with its design.

Premature deployment is therefore a problem. For example, the cannula may deploy when the device is placed on any site with slight pressure or when brushed against a surface such as a wrinkle in a pair of trousers. Deformed or misaligned parts may cause such unwanted premature deployment. Such premature activation, caused by the inadvertent application of a slight amount of pressure, is clearly unwanted.

Accordingly, there is a need for an improved automatic injector having a design that reduces the chances of a premature cannula deployment.

There are also a number of factors that can result in a failure of the cannula to deploy properly. For example, the cannula may fail to properly deploy if the auto-injector spring is weak, if the cannula is occluded, if a glass medicament-containing ampule breaks, if the piston sticks to the interior surface of the glass walls of the cartridge holder sleeve, if the device otherwise jams due to a parts misalignment, or the like.

A need therefore exists for an automatic injector having a design that reduces the chances of an improper cannula deployment.

Astronaut suits and other special clothing items include a special (self-sealing) area of the clothing designed to accept a cannula so that an emergency injection may be performed in the absence of a need to remove the clothing. The special area is small and not easy to hit when performing an emergency injection.

Thus there is a need for an automatic injector that would enable the user to position the leading end of the device in juxtaposition with an intended injection site before the needle is triggered.

Moreover, an automatic injector having means for shielding the deployed cannula is needed.

A good design also minimizes the use of natural resources, especially in devices that are used only once and discarded or re-cycled.

A need therefore exists for an automatic injector formed of less material than the automatic injectors of the prior art.

The medicament in an automatic injector may become cloudy due to age or some other cause. it may even leak out of the automatic injector if the ampule that contains such medicament has been damaged. When cloudy or discolored in any way, or if not present in its full effective quantity, the efficacy of the medicament is in doubt. Accordingly, pre-injection visual inspection of the medicament is required to ascertain whether or not it is present and suitable for use. Some of the known automatic injectors such as the EpiPen® have somewhat clear, semi-transparent parts that enable visual inspection of the medicament, but there are three layers of said parts (an outer cylindrical sleeve, a cartridge holder sleeve, and the medicament-containing ampoule). The outer cylindrical sleeve and the cartridge holder sleeve are formed of natural plastic and thus are semi-transparent. The ampoule is formed of clear glass. Thus, if either of the outer two parts become cloudy or otherwise lose at least some degree of transparency, visual inspection of the medicament is hindered.

Thus, there is a need for an automatic injector made of fewer parts so that pre-injection visual inspection of medicament does not require looking through three layers of parts.

An automatic injector can also fail because the medicament contained therewithin may fail to reach the tissue of the patient in whole or in part due to various mechanical malfunctions of the device. For example, it is possible for the cannula to deploy but for none of the medicament, or just a fraction thereof, to actually flow through the cannula into the patient's tissue.

Accordingly, there is a need for an automatic injector made of fewer parts so that post-injection visual inspection of medicament does not require looking through three layers of parts.

From a mechanical standpoint, the more parts a device has, the greater are the chances for a malfunction.

Thus there is also a need for an automatic injector having fewer parts to increase its reliability of operation.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for an automatic injector that is constructed of less materials, that has fewer parts, that may be positioned at a preselected location prior to release of the cannula, that provides sharps protection, and that otherwise advances the art is now met by a new, useful, and nonobvious invention.

A cartridge holder sleeve has a lumen that slideably receives a cartridge, a piston, a spring holder, and an inner gun sleeve. The cartridge is adapted to hold a liquid medicament. A cannula hub is mounted to a leading end of the cartridge, and a cannula is mounted to a leading end of the cannula hub. The piston is disposed in trailing relation to the cartridge and the spring holder is disposed in trailing relation to the piston.

A first diameter-reducing shoulder is formed in the cartridge holder sleeve near a leading end thereof. Accordingly, a reduced diameter section of said cartridge holder sleeve is formed in leading relation to said first diameter-reducing shoulder.

A spring-retaining shoulder is formed in the spring holder near a leading end thereof. The spring holder further includes a plurality of longitudinally extending parallel legs that extend in trailing relation to the shoulder.

A leading end of the inner gun sleeve is positioned within the lumen and a trailing end is positioned external to the lumen. In some embodiments, a truncate outer gun sleeve engages the trailing end of the inner gun sleeve. A safety cap is mounted to the outer gun sleeve, and said safety cap includes a safety pin that extends through a central aperture formed in the outer gun sleeve into a space surrounded by the parallel legs of the spring holder.

A piston biasing means under compression has a leading end disposed in abutting relation to the spring-retaining shoulder of the spring holder and a trailing end disposed in abutting relation to a trailing end of the inner gun sleeve. The trailing end of the inner gun sleeve is adapted to releasably engage the respective trailing ends of the parallel legs of the spring holder.

When the safety cap and hence the safety pin are removed, manual pressure applied against the outer gun sleeve in a trailing-to-leading direction effects radially inward travel of the parallel legs of the spring holder, thereby releasing the piston biasing means and driving the cannula into the tissue of the user.

The cannula, cartridge, piston, and spring holder are positioned within the lumen of the cartridge sleeve holder, toward the trailing end thereof in a retracted position, when the piston biasing means is under compression. Said parts slide abruptly toward the leading end of the lumen when the piston biasing means unloads. The cannula extends out of the lumen in leading relation to the leading end of the cartridge sleeve holder when the piston biasing means is in repose, i.e., not under compression.

In a first embodiment, a manually operated releasing means disengages the trailing end of the spring holder from the trailing end of the inner gun sleeve so that the piston biasing means unloads when the releasing means is activated. The structure of the first embodiment eliminates the outer cylindrical sleeve of the automatic injector disclosed in the above-mentioned expired patent.

In a second embodiment, a sharps protector is mounted to the cartridge holder sleeve on the reduced-diameter section thereof.

The sharps protector has a first, retracted position where a leading end of the sharps protector is substantially co-extensive with a leading end of the cannula when the cannula is in a retracted position. The sharps protector has a second, extended position where a leading end of the sharps protector is substantially co-extensive with a leading end of the cannula when the cannula is in an extended position.

A user of the automatic injector manually displaces the sharps protector from the first, retracted position to the second, extended position after the release means has been activated.

More particularly, an annular detent means is formed in a trailing end of the manually operated sharps protector. A first annular recess is formed in the reduced diameter part of the cartridge holder sleeve, and the first annular recess receives the annular detent means when the sharps protector is in its retracted configuration. A second annular recess is formed in said reduced diameter part of the cartridge holder sleeve in leading relation to the first annular recess. The second annular recess receives the annular detent means when the sharps protector is manually displaced into its extended configuration.

In a third embodiment, a second diameter-reducing annular shoulder is formed in the reduced diameter section of the cartridge holder sleeve in leading relation to the first diameter-reducing shoulder and a diameter-reducing taper is formed in the reduced diameter section of the cartridge holder sleeve in leading relation to the second diameter-reducing shoulder. The second diameter-reducing shoulder provides a stop means for the trailing end of an internally mounted sharps protector biasing means, which may take the form of a coil spring, for automatically deploying the sharps protector.

The sharps protector biasing means has a lumen that receives the downwardly-tapered leading end of the cartridge holder sleeve. The sharps protector biasing means has a trailing end that abuts the second diameter-reducing shoulder and a leading end that abuts the leading end of the sharps protector, internally thereof.

In the third embodiment; a first latch means, formed of a pair of diametrically opposed first latch members, is formed in a trailing end of the sharps protector and is separated from the sharps protector along a parting line at a leading end and opposite sides of each first latch member. A trailing end of each first latch member forms a living hinge with the sharps protector and the leading end of each first latch member extends into a first catch means to prevent unloading of the sharps protector biasing means. The first catch means includes a pair of diametrically opposed slots or catch members formed in the reduced diameter section of the cartridge holder sleeve.

Accordingly, retraction of the leading end of each first latch member from its associated first catch member enables unloading of the sharps protector biasing means and deployment of the sharps protector to its fully extended position where the deployed cannula is fully housed therewithin.

A pair of diametrically opposed accommodation slots is formed in the sharps protector in spaced apart, leading relation to the first catch members. A stop means includes a pair of diametrically opposed stop members. Each stop member is separated from the sharps protector along a parting line at a trailing end and opposite sides of each stop member, leaving a living hinge at the leading end of each stop member. The trailing end of each stop member extends into its associated accommodation slot when the sharps protector biasing means is under load and the sharps protector is in its retracted position. The trailing end of each stop member extends into its associated second catch member when the sharps protector biasing means is unloaded and the sharps protector is in its deployed position, thereby preventing displacement of the sharps protector in a leading-to-trailing direction.

A pair of diametrically opposed elongate guide slots are also formed in the reduced diameter section of the cartridge holder sleeve. A pair of diametrically opposed detent means is formed in the trailing end of the sharps protector. Each detent means slideably engages an associated guide slot.

In a fourth embodiment, the trailing end of an externally mounted sharps protector biasing means abuts the first diameter-reducing annular shoulder and the leading end of the externally mounted sharps protector biasing means abuts the trailing end of the sharps protector. The arrangement of latch members, catch members, stop members, and detents that control operation of the third embodiment also forms a part of the fourth embodiment.

An important object of this invention is to improve the design and hence lower the cost of conventional automatic injectors by substantially reducing the amount of materials used to make them.

Another important object of this invention is to provide an automatic injector having manually deployable means for covering a deployed cannula.

Still another important object is to provide an automatic injector having automatically deployable means for covering a deployed cannula.

Yet another object is to provide different embodiments of the automatic injector so that in a first embodiment the cannula may be placed into position with an injection site prior to activation of the cannula extending means and so that in a second embodiment the act of delivering the leading end of the auto injector to the injection site results in automatic deployment of the cannula.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2 is a longitudinal sectional view of a first embodiment of the invention;

FIG. 3 is an exploded perspective view of some of the parts of said first embodiment;

FIG. 4 is a transverse sectional view taken along line 4—4 in FIG. 2;

FIG. 5 is a sectional view of the manually deployable sharps protector when in its undeployed configuration;

FIG. 6 is a longitudinal sectional view taken along line 6—6 in FIG. 5;

FIG. 7 is a longitudinal sectional view of the sharps protector of FIG. 5 when in its deployed configuration;

FIG. 8 is a longitudinal sectional view of an embodiment of the manually deployable sharps protector having an elongated inner gun sleeve when the cannula is in its undeployed configuration;

FIG. 9 is a longitudinal sectional view of an embodiment where the sharps protector is deployable by a sharps protector biasing means mounted within the sharps protector and where neither the cannula nor the sharps protector are deployed;

FIG. 10 is a transverse sectional view taken along line 10—10 in FIG. 9;

FIG. 11 is a longitudinal sectional view like that of FIG. 10 but where the cannula is deployed and the automatically deployable sharps protector remains undeployed;

FIG. 12 is a transverse sectional view taken along line 12—12 in FIG. 11;

FIG. 13 is a longitudinal sectional view like that of FIG. 11 but where both the cannula and the sharps protector are deployed;

FIG. 14 is a longitudinal sectional view of an embodiment of the novel automatic injector where a sharps protector biasing means for automatically deploying the sharps protector is mounted externally of the sharps protector;

DETAILED DESCRIPTION

Figure 1A:
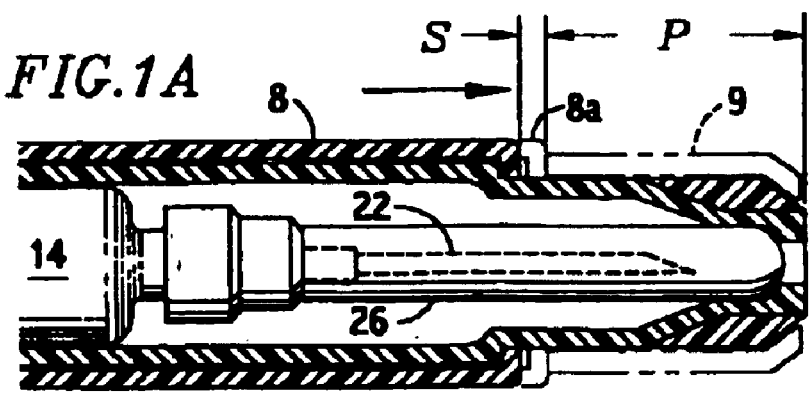
FIG. 1A is a longitudinal sectional view of the leading end of a prior art auto-injector when an unillustrated piston biasing means is loaded.

Referring first to prior art FIG. 1A, it will there be seen that the stroke of the outer cylindrical sleeve 8 of the EpiPen® auto-injector and its military counterpart, the Pralidoxime ComboPen, is denoted by a pair of confronting arrows labeled by the letter "S." The in-repose position of outer cylindrical sleeve 8 is cross-hatched and the momentary forward position said sleeve 8 attains when the user activates the device is depicted in unhatched lines and is denoted 8a.

Figure 1B:
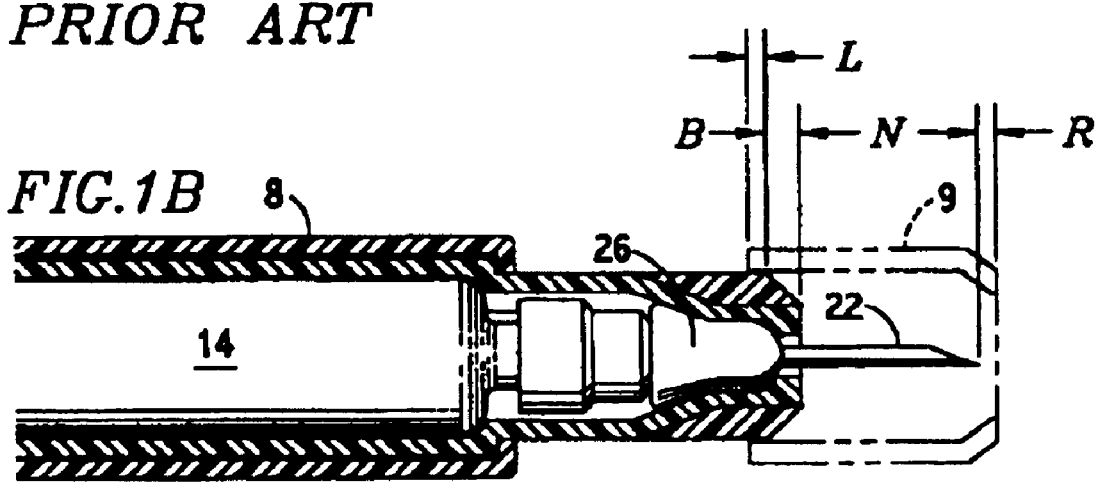
FIG. 1B is a view like that of FIG. 1A but when the unillustrated piston biasing means has been unloaded, driving the cannula into its deployed position.

When needle 22 is deployed, as depicted in FIG. 1B, outer cylindrical sleeve 8 returns to its FIG. 1A in-repose position after only momentarily attaining said 8a position.

The EpiPen® auto injector and its military counterpart both lack sharps protection as mentioned earlier. If a sharps protector were simply retrofit onto said devices, as indicated in FIG. 1A, only the distance denoted "P" would be available to accommodate said sharps protector, depicted in phantom lines and denoted 9, and said distance would be clearly inadequate for the reasons that follow.

Distance "P" is measured from an unnumbered annular shoulder to the distal free end of the auto injector. Said annular shoulder is positioned about mid-way of the length of cannula 22, radially outwardly thereof, when said cannula 22 is in its FIG. 1A retracted or undeployed position. The leading end of cartridge 14 is substantially co-extensive with said annular shoulder, radially outwardly thereof, when cannula 22 is extended or deployed as depicted in FIG. 1B.

As further indicated in FIG. 1B, if hypothetical sharps protector 9 were manually deployed, only a very short length thereof, denoted "L," would be available to engage the trailing end of said sharps protector. Sharps protector 9 would thus not be securely attached to the auto injector and could not be relied upon to perform its intended function. The length denoted "B" indicates a bevel formed in the leading end of the auto injector; said beveled area is not available as a mounting surface for sharps protector 9. The distance denoted "R" is the amount by which cannula 22 is recessed from the distal end of sharps protector 9 when said cannula 22, having an exposed length denoted "N," is deployed. Recess "R" would be inadequate to protect the sharp distal end of cannula 22 in all handling situations because it is shallow.

If a sharps protector were simply retrofit onto the EpiPen® and its military counterpart, the approximate dimensions of the above-described distances would be as follows: Stroke distance "S" would be about 0.09 inches; Protector-accommodating distance "P" would be about 0.89 inches; Accommodating length "L" would be about 0.06 inches; Beveled distance "B" would be about 0.12 inches; Exposed needle length "N" would be about 0.65 inches; and Recess "R" length would be about 0.06 inches. Thus, it would not have been obvious to add a sharps protector to such devices because the dimensions thereof are inadequate to adequately support a sharps protector. Nor would it have been obvious to re-design such devices so that they could accommodate a sharps protector because such re-designing could not be accomplished by a mere enlarging of the dimensions of the devices.

Referring now to FIGS. 2–4, it will there be seen that the reference numeral 10 denotes an illustrative embodiment of the novel automatic injector. This first embodiment improves upon the devices of the prior art but does not include a sharps protector.

By comparing FIG. 2 with FIGS. 1A and 1B, it will be observed that outer cylindrical sleeve 8 is eliminated, thereby saving materials and eliminating the need to aim the auto injector carefully at a target injection site. It will also be observed that the unnumbered annular shoulder against which the leading end of said sleeve 8 abuts is eliminated, thereby freeing up a large extent of the auto injector for accommodating a sharps protector.

Automatic injector 10 includes cartridge holder sleeve 12 having lumen 13. A reduced-diameter section 15 of cartridge holder sleeve 12 is formed by first diameter-reducing annular shoulder 17. Annular shoulder 17 is set far back from leading end 12a of cartridge holder sleeve 12. However, it should be understood from the outset that annular shoulder 17 is an optional, i.e., non-critical feature of the novel device and the benefits of the invention may be realized even if said annular shoulder is eliminated. Where shoulder 17 is obviated, a plurality of radially outwardly projecting splines, not shown, or other suitable stop means, could perform the stop function of said shoulder.

Lumen 13 slideably receives cartridge 14 that is filled with liquid medicament 16.

When slideably-mounted piston 18 is displaced in a trailing-to-leading direction, as indicated by single-headed directional arrow 20, liquid medicament 16 is expelled from cartridge 14 so that it flows into cannula 22.

Cartridge 14 is interconnected to cannula 22 by cannula hub 24. Flexible and resilient sheath 26 houses cannula 22. Sheath 26 has a closed distal end 28.

Spacer 30 has head 31 that snaps into and engages the open trailing end of piston 18. Annular, radially inwardly-turned flange 36 formed in the trailing end of piston 18 extends radially inwardly into the open trailing end of piston 18 and prevents retraction of head 31 from said open trailing end.

Head 34 of spring holder 32 has a frusto-conical shape and is formed of a material that is harder than the material of which spacer 30 is formed so the trailing annular edge of frusto-conical head 34 digs into the cylindrical blind bore formed in the trailing end of spacer 30, thereby securing head 34 within said cylindrical blind bore. Spring holder 32 and its head 34 are preferably of metallic construction and spacer 30 is preferably of plastic construction.

As best understood in connection with FIG. 3, shoulders 40 formed in spring holder 32 have leading surfaces, collectively denoted 40a, that abut the trailing end of spacer 30 and trailing surfaces, collectively denoted 40b, against which abuts leading end 42a of a piston biasing means which may take the form of coil spring 42 or an equivalent piston biasing means.

Inner gun sleeve 44 (FIG. 2) substantially houses piston biasing means 42. Trailing end 42b of piston biasing means 42 abuts leading radially inwardly turned wall 46 of inner gun sleeve 44. Accordingly, piston biasing means 42 is held in compressed relation between said inwardly turned wall 46 and trailing surfaces 42b of shoulders 40 of spring holder 32.

An annular radially outwardly extending detent 45 is formed in inner gun sleeve 44 about mid-length thereof and said detent engages an unnumbered corresponding annular recess formed in an interior cylindrical wall of cartridge holder sleeve 12. This interconnects said inner gun sleeve 44 and cartridge holder sleeve 12.

In this embodiment, annular radially outwardly extending detent 47 is formed in inner gun sleeve near the trailing end thereof.

Metal washer 48 is part of the assembly that prevents piston biasing means 42 from unloading when automatic injector 10 is not in use. The outer periphery of washer 48 is captured by a washer-gripping member that includes leading radially inwardly turned wall 46 and trailing radially inwardly turned wall 50. An annular washer-retaining recess is defined between said two walls. The annular recess is unnumbered to avoid cluttering the drawings.

Spring holder 32 includes a plurality of equidistantly and circumferentially spaced apart legs, collectively denoted 52, that are disposed in parallel relation to one another. Each leg has a radially outwardly turned detent 54 formed near its trailing end. A recess 55 is formed in each leg 52 on the leading side of each detent 54. The inner periphery of metal washer 48, i.e., the part of said metal washer that borders its central aperture, bears against the leading side of said detents, i.e., extends into each recess 55, and therefore prevents trailing-to-leading displacement of spring holder 32 by piston biasing means 42.

Spring holder 32 is preferably made of a metallic material that exhibits flexibility and resilience. Accordingly, radially inward travel of legs 52 disengages detents 54 from the inner peripheral edge of washer 48, thereby allowing piston biasing means 42 to unload and to drive piston 18 and hence cannula 22 in a trailing-to-leading direction as denoted by arrow 20 as aforesaid, thereby administering liquid medicament 16 to the tissue of the user.

When auto injector 10 is not in use, such radially inward travel of legs 52 is barred by safety pin 56 that extends into the space surrounded by legs 52. Safety pin 56 is formed integrally with cap 58 and is coincident with the longitudinal axis of symmetry of automatic injector 10.

In this embodiment, outer gun sleeve 60 is a cap-like member of truncate configuration having an unnumbered central aperture formed therein to accommodate safety pin 56. Clearance space 62 at the leading end of outer gun sleeve 60 and the trailing end of cartridge holder sleeve 12 enables displacement of outer gun sleeve 60 in the direction of arrow 20 when cap 58 is removed.

Leading end of truncate outer gun sleeve 60 has an annular, radially-inwardly turned detent 61 formed therein that is positioned on the leading side of the annular radially-outwardly turned detent 47 formed in inner gun sleeve 44 to interlock said inner and outer gun sleeves.

As will become more clear as this disclosure proceeds, truncate outer gun sleeve 60 may also take the form of an elongate outer gun sleeve 60a, denoted in phantom lines in FIG. 2. In that structural variation, outer gun sleeve 60 does not end at clearance space 62 but instead turns radially outwardly and partially ensleeves cartridge holder sleeve 12. Outer gun sleeve 60a could extend nearly to shoulder 17, but in a preferred embodiment, as depicted, it stops short of said shoulder to enhance the visibility of liquid medicament 16, i.e., a user may inspect said medicament without looking through said outer gun sleeve 60a.

A bead or protrusion is formed in surrounding relation to the central aperture formed in outer gun sleeve 60, on the leading side of said central aperture, and an annular beveled surface 64 is formed in said bead or protrusion. Note in FIG. 2 that said annular beveled surface abuts against the respective beveled surfaces of detents 54 formed in the trailing end of spring holder 32, and that beveled surfaces 54 and 64 are slidingly engaged to one another. Accordingly, when a user's thumb presses on outer gun sleeve 60 in the direction of arrow 20, detent 64 drives detents 54 radially inwardly toward one another. Leading surface 54a (FIG. 3) of each detent 54 is thus displaced radially inwardly until each of said leading surfaces disengage from washer 48. Such disengagement allows piston biasing means 42 to unload and piston 18, cartridge 14, and cannula 22 are driven in the direction of arrow 20, thereby administering liquid medicament 16 to the user's tissue through cannula 22.

Circumferentially spaced apart cartridge stops 66 extend radially inwardly into the lumen of cartridge holder sleeve 12 and perform the function their name expresses when piston biasing means 42 unloads. Cannula 22 pierces distal end 28 of sheath 26 when piston biasing means 42 unloads, but sheath 26 serves to cushion the impact of cartridge 14 as it is abruptly displaced in a trailing-to-leading direction.

Cartridge stops 66 are not a critical feature of the invention and may be eliminated by reducing the diameter of lumen 13 of cartridge holder sleeve 12 at the location of said cartridge stops 66. More particularly, a lumen-diameter-reducing shoulder would be formed in lumen 13 at the trailing end of said stops 66.

Turning now to FIGS. 5–8, wherein a second embodiment of the invention is disclosed, it will there be seen that the novel manually-operated sharps protector of this embodiment is denoted 70 as a whole. It is generally cylindrical in configuration and has a diameter-reducing frusto-conical leading end 72.

An annular, radially inwardly extending detent 74 is formed in the trailing end of sharps protector 70. When in its retracted, undeployed configuration, as depicted in FIG. 5, annular detent 74 is engaged with first annular recess 76 (depicted in FIG. 5 and numbered in FIG. 7) formed in cartridge holder sleeve 12. When in its extended, deployed configuration, as depicted in FIG. 7, annular detent 74 is engaged with second annular recess 77 (depicted in FIG. 7 and numbered in FIG. 5), said second annular recess 77 being formed in cartridge holder sleeve 12 closer to its leading end than first annular recess 76. Displacement of sharps protector 70 from the FIG. 5 position to the FIG. 7 position is performed manually.

Sheath 26 is depicted in its in-repose configuration in FIG. 5 and in its compressed configuration in FIG. 7, indicating that in FIG. 7 piston biasing means 42 is in its unloaded configuration and that cannula 22 is in its extended position.

FIG. 8 depicts a variation of the second embodiment where truncate outer gun sleeve 60 (FIG. 2) is replaced by elongate outer gun sleeve 60a. As best understood in connection with FIG. 2, elongate outer gun sleeve 60a is disposed in housing relation to cartridge holder sleeve 12, stopping on the trailing side of shoulder 17. The provision of elongate outer gun sleeve eliminates annular radially outwardly turned detent 47 formed in inner gun sleeve 44 near its trailing end as depicted in FIG. 2 and also eliminates annular radially inwardly turned detent 61 formed in truncate outer gun sleeve 60 that interlocks with said detent 47 as depicted in FIG. 2. Note that elongate gun sleeve 60a is sufficiently short so as not to cover the leading end of medicament-containing ampoule or cartridge 14, thereby enhancing pre-firing inspection of said medicament.

Annular radially outwardly disposed detent 47 is re-located as depicted in FIG. 8 to the leading end of cartridge holder sleeve 12, on the trailing side of shoulder 17.

Annular recess 63 is formed on an internal surface of elongate outer gun sleeve 60a to receive said annular detent 47. As illustrated, annular recess 63 has a longitudinal extent sufficient to accommodate detent 47 and to allow longitudinal displacement of said elongate outer gun sleeve 60a relative to cartridge holder sleeve 12 when said elongate outer gun sleeve is displaced in a trailing-to-leading direction to release piston biasing means 42. Detent 47 abuts the leading end of recess 63 when piston biasing means 42 is loaded and the trailing end of said recess when said piston biasing means is unloaded.

The relocation of detent means 47 and the elimination of detent means 61, as best understood by comparing FIGS. 2 and 8, simplifies the structure of the novel auto injector. Moreover, it enables a user to circumferentially grasp elongate outer gun sleeve 60a with a hand and to drive leading end 12a of cartridge holder sleeve 12 onto a target injection site, just as is done with the aforementioned EpiPen® auto injector of the prior art. Significantly, since the leading end of elongate outer gun sleeve 60a does not extent past shoulder 17, said elongate outer gun sleeve does not infringe upon the space provided on the leading side of said shoulder to accommodate sharps protector 70 or 80.

In the third embodiment of the invention, depicted in FIGS. 9–13, an internally mounted sharps protector biasing means, preferably in the form of coil spring 78, is employed to deploy a second embodiment of the sharps protector, denoted 80.

A second diameter-reducing shoulder 19 is formed in said cartridge holder sleeve in leading relation to first diameter-reducing shoulder 17. A diameter-reducing taper 19a is formed in cartridge holder sleeve 12 in leading relation to diameter-reducing shoulder 19. Diameter-reducing taper 19a forms a tapered section of said cartridge holder sleeve. Sharps protector biasing means 78 has a lumen that receives said tapered section therein. Sharps protector biasing means 78 has a trailing end that abuts diameter-reducing shoulder 19 and has a leading end that abuts the leading end of sharps protector 80.

As best understood in connection with FIGS. 9–13, four sets of slot-shaped openings or catch means are formed in reduced diameter section 15 of cartridge holder sleeve 12. First catch means 82 and accommodation slot 84 are separated from one another by annular part 15a of section 15. Accommodation slot 84 is formed in section 15 in leading relation to first catch means 82 and second catch means 92 is formed in section 15 in leading relation to accommodation slot 84. Guide slot 86 is formed in section 15 in circumferentially spaced relation to first catch means 82, accommodation slot 84, and second catch means 92.

Figure 17:
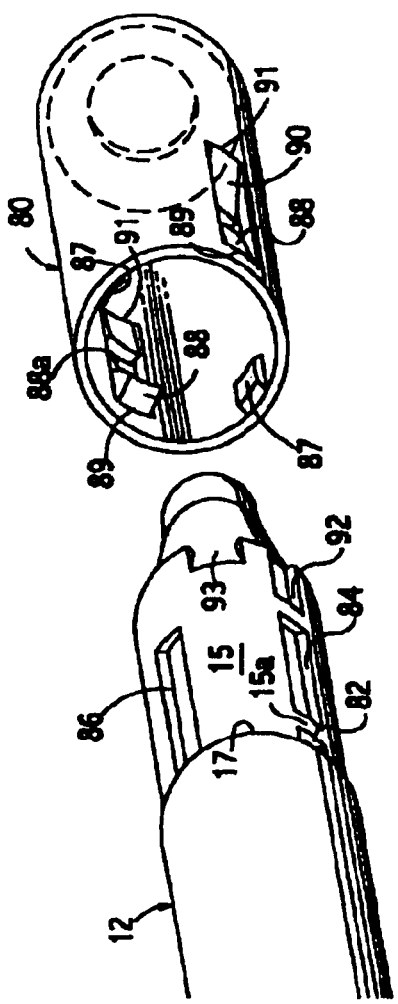
FIG. 17 is an exploded perspective view of the leading end of the cartridge holder sleeve and the sharps protector.

As perhaps best understood in connection with FIG. 17, first catch means 82 is provided in the form of two first catch members 82, 82 that are positioned in diametric opposition to one another. Moreover, there are two accommodations slots 84, 84 in diametric opposition to one another. Second catch means 92 is provided in the form of two second catch members 92, 92 that are positioned in diametric opposition to one another, and there are two guide slots 86, 86 in diametric opposition to one another.

A pair of diametrically opposed, radially inwardly projecting detents 87, 87, best depicted in FIG. 17, is formed integrally with the trailing end of sharps protector 80 and respectively slideably engage elongate guide slots 86, 86. More particularly, detents 87, 87 abut the respective trailing ends of guide slots 86, 86 when sharps protector biasing means 78 is under compression and sharps protector 80 is in its retracted position as depicted in FIGS. 9 and 11.

Detents 87, 87 abut the leading end of guide slots 86, 86 when sharps protector biasing means 78 is in repose and sharps protector 80 is in its fully extended, deployed configuration as depicted in FIG. 13.

As best understood in connection with FIGS. 9 and 17, each latch means 88, 88 is punched out of sharps protector 80 so that a trailing end 89, 89 thereof remains secured to said sharps protector and forms a living hinge therewith. More particularly, each latch means 88, 88 is cut away from sharps protector 80 along a transverse parting line at its leading end, by a longitudinal parting line at each of its opposite sides, and remains connected to said sharps protector along said transversely disposed living hinge at its trailing end.

Leading end 88a of each latch means 88 is positioned in abutting relation to the leading end of first catch means 82 as depicted in FIG. 9 when sharps protector biasing means 78 is under compression and sharps protector 80 is in its retracted, undeployed configuration.

As depicted in FIG. 11, leading end 88a of each latch means 88 is disengaged from the leading end of its associated catch means 82 but sharps protector biasing means 78 has not unloaded because leading end 12a of cartridge holder sleeve 12 is disposed in abutting relation with a user's tissue 100, thereby preventing unloading of sharps protector biasing means 78 even though the trailing end of sharps protector 80 is no longer retained by latch means 88, 88.

As depicted in FIG. 13, cannula 22 has been withdrawn from tissue 100, thereby allowing sharps protector biasing means 78 to unload and push sharps protector 80 into its fully extended, deployed position.

A pair of stop means 90, 90 is also punched out of said sharps protector 80, each stop means 90 having a leading end 91 secured to said sharps protector to form a living hinge therewith. Each stop means 90 is biased to bend radially inwardly so that its trailing end abuts the trailing end of its associated accommodation slot 84 when sharps protector biasing means 78 is under load and sharps protector 80 is in its retracted, undeployed position.

As best understood by comparing FIGS. 9 and 11 with FIG. 13, each stop means 90 exits its associated accommodation slot 84 when sharps protector biasing means 78 unloads. However, since it is biased radially inwardly as aforesaid, each stop means 90 slides along the exterior surface 15 of the reduced diameter section of cartridge holder sleeve 12 until it encounters second catch means 92. The trailing end of each stop means 90, under its inherent bias, displaces radially inwardly to engage the trailing end of each second catch means 92 as depicted in FIG. 13.

As depicted in FIG. 13, pressure applied to the leading end of sharps protector 80 in the direction of arrow 20a will not cause displacement of said sharps protector in the direction of said arrow 20a because the trailing end of each stop means 90 is disposed in abutting relation to the trailing shoulder of its associated second catch means 92. This ensures that upon deployment of sharps protector 80, it cannot be driven in a leading-to-trailing direction by pressure applied in said direction.

When cartridge 14 is propelled in the direction of arrow 20 by the means disclosed hereinabove, said cartridge contacts and displaces each latch means 88, 88 from its FIG. 9 position to its FIG. 11 position, i.e., it pushes said latch means radially outwardly. Accordingly, leading end 88a of each latch means 88, 88 disengages from section 15a of cartridge holder reduced diameter section 15, i.e., disengages from the leading end of first catch means 82, thereby freeing sharps protector biasing means 78 to unload.

Ramp 93 (FIG. 17) is provided to facilitate the initial assembly of automatic injector 10. Radially inwardly biased stop means 90 is aligned with ramp 93 when sharps protector 80 is mounted onto the leading end of cartridge sleeve holder 12 during assembly so that said radially-inwardly biased stop means 90 slides up said ramp 93 onto surface 15 which is the reduced diameter part of cartridge sleeve holder 12 that is in leading relation to shoulder 17 as aforementioned. Sharps protector 80 is then rotated about its longitudinal axis of symmetry until detents 87, 87 enter into engagement with guide slots 86, 86, latch means 88, 88 enters into engagement with first catch means 82, 82, and stop means 90, 90 enter into engagement with accommodation slots 84, 84.

Figure 15:
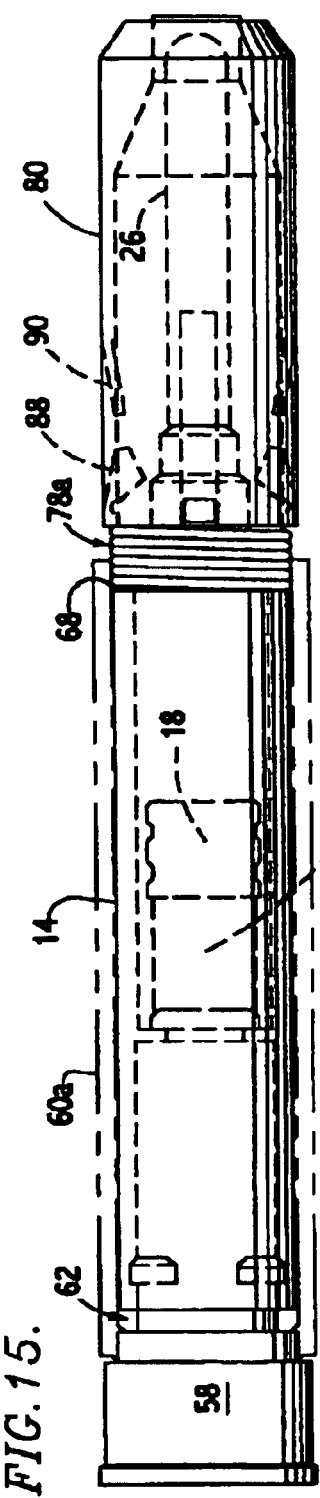
FIG. 15 is a side elevational view of an alternative embodiment of the FIG. 14 embodiment, depicting an elongated inner gun sleeve in phantom lines.
Figure 16:
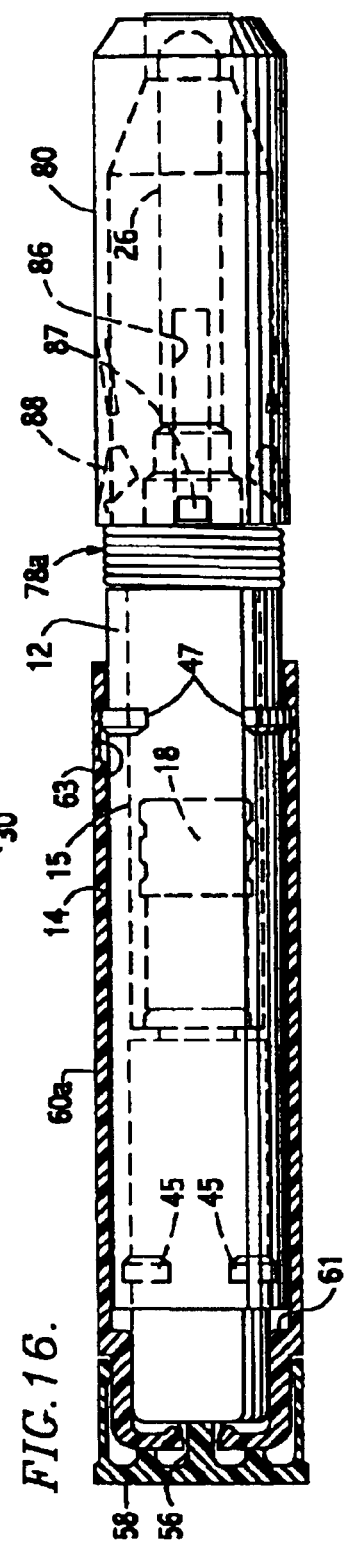
FIG. 16 is a view like FIG. 15 depicting a shortened version of the elongated gun sleeve to enhance pre-firing visual inspection of the medicament.

The fourth embodiment of the invention is depicted in FIGS. 14–16. The embodiment of FIGS. 14–16 differs from the preceding embodiment of FIGS. 9–13 in that sharps protector biasing means 78a is mounted externally of sharps protector 80. Specifically, sharps protector biasing means 78a has a leading end disposed in abutting relation to a trailing end of sharps protector 80 and a trailing end in abutting relation to shoulder 17.

As indicated by comparing FIG. 15 and FIG. 16 to one another, spring 78a may be substantially covered when a longer version of elongate outer gun sleeve 60a is employed (FIG. 15, with elongate gun sleeve 60a in phantom lines) and may be uncovered when a shortened version of elongate outer gun sleeve 60a is provided (FIG. 16, with elongate outer gun sleeve 60a depicted in longitudinal section). The purpose of the shortened version of elongate outer gun sleeve 60a, as mentioned earlier, is to enhance the pre-firing visual inspection of the medicament contained within ampoule or cartridge 14.

Sharps protector biasing means 78a of this embodiment is triggered in substantially the same way as sharps protector biasing means 78 of the internally-mounted spring embodiment.

In the embodiment of FIG. 16, annular radially outwardly extending detent 47 is formed in cylinder holder sleeve 12 near the leading end thereof. Annular recess 63 formed in the interior cylindrical wall of cartridge holder sleeve 12 receives said detent 47 just as in the preceding embodiment.

The ability to release piston biasing means 42 by pressing on outer gun sleeve 60 after removing safety cap 58 is made possible by eliminating the outer cylindrical sleeve of the prior art automatic injector. The ability to release piston biasing means 42 after first positioning leading end 12a of cartridge holder sleeve 12 on an injection target site is also made possible by said improvement. Elimination of such outer cylindrical sleeve saves a substantial amount of materials and further enables the provision of an elongate reduced diameter section 15 of cylindrical sleeve holder 12 that provides ample mounting space for a sharps protector. The new design also greatly reduces the longitudinal extent of the outer gun sleeve, thereby further saving materials and enhancing pre-firing inspection of medicament by eliminating a layer of plastic to look through. The provision of a manually deployed or an automatically deployed sharps protector for an automatic injector, made possible by said improvements, also represents a significant advance in the art.

Moreover, where an outer gun sleeve is lengthened to enable circumferential grasping of the device, a shortened version of said elongated outer gun sleeve enhances pre-firing medicament inspection.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. An automatic injector, comprising:
a transparent cartridge holder sleeve having a leading end and a an open trailing end;
said leading end having a diameter that does not exceed a diameter of said transparent cartridge holder sleeve;
said cartridge holder sleeve having a lumen;
a cartridge adapted to hold a liquid medicament;
a cannula hub mounted to a leading end of said cartridge;
a cannula mounted to a leading end of said cannula hub;
a piston disposed in trailing relation to said cartridge;
a spacer disposed in trailing and engaging relation to said piston;
a spring holder disposed in trailing and engaging relation to said spacer;
a spring-retaining shoulder formed in said spring holder near a leading end thereof;
said cartridge, piston, and spring holder being slideably received within said lumen;
an inner gun sleeve having a leading end positioned within said lumen, said inner gun sleeve secured to said cartridge holder sleeve at said open trailing end of said cartridge sleeve;
a piston biasing spring under compression having a leading end disposed in abutting relation to said spring-retaining shoulder of said spring holder and a trailing end disposed in abutting relation to a trailing end of said inner gun sleeve;
said trailing end of said inner gun sleeve adapted to releasably engage a trailing end of said spring holder;
said cartridge, piston, spring holder, and cannula being positioned within said lumen in a retracted position when said piston biasing spring is under compression;
said cartridge, piston, and spring holder being positioned within said lumen in an extended position and said cannula extending out of said lumen in leading relation to said cartridge sleeve holder when said piston biasing spring is in repose; and
manually operated releasing means for disengaging said trailing end of said spring holder from said trailing end of said inner gun sleeve so that said piston biasing spring unloads when said releasing means is activated;
said manually operated releasing means including manual displacement of said inner gun sleeve in a trailing-to-leading direction;
a sharps protector movably mounted to said leading end of said cartridge holder sleeve and having a retracted position and an extended position;
said sharps protector being in said retracted position when said cannula of said automatic injector is in a retracted position;
said sharps protector being in said extended position when said cannula is in an extended position;
said sharps protector when in said retracted position having a length sufficient to extend beyond a distal end of said cannula when said cannula is in said retracted position; and
said sharps protector when in said extended position having a length sufficient to extend beyond a distal end of said cannula when said cannula is in said extended position.

2. The automatic injector of claim 1, further comprising:
said spring holder including at its trailing end a plurality of longitudinally-extending, parallel leg members;
said parallel leg members having respective positions of repose where each parallel leg member is parallel to each other leg member of said plurality of parallel leg members;
each of said parallel leg members having sufficient flexibility to enable them to be deflected radially inwardly;
an outer gun sleeve of truncate extent having a radially-inwardly extending detent formed in a leading end thereof;
said inner gun sleeve having a radially-outwardly extending detent disposed in trailing, abutting relation to said outer gun sleeve radially-inwardly extending detent;
a clearance space disposed between said leading end of said outer gun sleeve and a trailing end of said cartridge holder sleeve to enable trailing-to-leading displacement of said outer gun sleeve.

3. The automatic injector of claim 2, further comprising:
a bevel formed in each trailing end of each of said parallel leg members;
a recess formed in each parallel leg member adjacent each bevel in leading relation thereto;
a trailing leg detent are engaged by said inner gun sleeve trailing end;

said trailing leg detent extending into the recess formed in each of said parallel leg members and preventing trailing-to-leading displacement of said parallel leg members when in their respective positions of repose.

4. The automatic injector of claim 3, further comprising:

a central aperture formed in said outer gun sleeve;

a safety cap that engages said outer gun sleeve;

said safety cap having a longitudinally-extending stop member that extends through the central aperture formed in said outer gun sleeve;

said stop member being surrounded by said parallel leg members and said stop member preventing radially-inwardly directed displacement of said parallel leg members;

said parallel leg members being displaceable in a radially-inwardly direction when said safety cap member is removed from said outer gun sleeve.

5. The automatic injector of claim 4, further comprising:

an annular protuberance formed on said outer gun sleeve in surrounding relation to said central aperture on a leading side of said central aperture;

an annular bevel formed in said protuberance;

said annular bevel adapted to slideably engage each bevel formed on the trailing end of said parallel legs when said outer gun sleeve is manually displaced in a trailing-to-leading direction to thereby drive each leg of said parallel legs radially inwardly;

whereby each leg of said parallel legs disengages from said trailing leg detent;

whereby said piston biasing spring unloads and drives said piston and hence said cannula in a trailing-to-leading direction.

6. The automatic injector of claim 1, further comprising:

a sharps protector movably mounted to said leading end of said cartridge holder sleeve and having a retracted position and an extended position;

said sharps protector being in said retracted position when said cannula of said automatic injector is in a retracted position;

said sharps protector being in said extended position when said cannula is in an extended position;

said sharps protector when in said retracted position having a length sufficient to extend beyond a distal end of said cannula when said cannula is in said retracted position; and said sharps protector when in said extended position having a length sufficient to extend beyond a distal end of said cannula when said cannula is in said extended position.

7. The automatic injector of claim 1, further comprising:

a first diameter-reducing shoulder formed in said cartridge sleeve holder;

said cartridge sleeve holder having a reduced diameter part in leading relation to said first diameter-reducing shoulder;

a sharps protector detent formed in a trailing end of said sharps protector;

a first recess formed in said reduced diameter part of said cartridge holder sleeve, said first recess receiving said sharps protector detent when said sharps protector is in its retracted configuration;

a second recess formed in said reduced diameter part of said cartridge holder sleeve, said second recess disposed in leading relation to said first recess and said second recess receiving said sharps protector detent when said sharps protector is in said extended configuration;

whereby said sharps protector is manually displaceable from engagement with said first recess to engagement with said second recess when said cannula has been displaced from said retracted to said extended position.

8. The automatic injector of claim 7, wherein said sharps protector detent, said first recess, and said second recess are of annular configuration.

9. The automatic injector of claim 1, further comprising:

a first diameter-reducing shoulder formed in said cartridge sleeve holder;

said cartridge sleeve holder having a reduced diameter part in leading relation to said first diameter-reducing shoulder;

a second diameter-reducing shoulder formed in said reduced diameter section of said cartridge holder sleeve in leading relation to said first diameter-reducing shoulder;

said reduced diameter section of said cartridge holder sleeve having a diameter-reducing taper formed in its leading end, said diameter-reducing taper being formed in leading relation to said second diameter-reducing shoulder, and said diameter-reducing taper forming a tapered section of said cartridge holder sleeve;

an internally-mounted sharps protector biasing spring under compression having a lumen that receives said tapered section therein;

said internally-mounted sharps protector biasing spring having a trailing end that abuts said second diameter-reducing shoulder and a leading end that abuts said leading end of said sharps protector;

a first catch formed in said reduced diameter section of said cartridge holder sleeve;

a latch formed in a trailing end of said sharps protector, said latch disposable in releasable engagement with said catch when said sharps protector is in its retracted position;

said latch adapted to be unlatched when said main piston biasing spring unloads and drives said cartridge in a trailing-to-leading direction;

whereby unlatching of said latch releases said latch from said catch so that said compressed sharps protector biasing spring unloads and displaces said sharps protector from said retracted position to said extended position.

10. The automatic injector of claim 9, wherein said first catch includes a pair of diametrically opposed catch members formed in said leading end of said reduced diameter section of said cartridge holder sleeve.

11. The automatic injector of claim 10, wherein said latch includes a pair of diametrically opposed latch members formed in a trailing end of said sharps protector.

12. The automatic injector of claim 11, further comprising:

each of said latch members being separated from said sharps protector along a parting line at a leading end and opposite sides of said latch members;

a trailing end of each of said latch members forming a living hinge with said sharps protector; and each latch member having a leading end extending into said first catch to prevent unloading of said sharps protector biasing spring;

whereby retraction of each leading end of each latch member from its associated first catch enables unloading of said sharps protector biasing and deployment of said sharps protector to its fully extended position where said deployed cannula is fully housed therewithin.

13. The automatic injector of claim 12, further comprising:
   a pair of accommodation slots formed in said reduced diameter section of said cartridge holder sleeve, said accommodation slots being diametrically opposed with respect to one another and each accommodation slot being disposed in spaced apart, leading relation to an associated first catch member;
   a pair of radially inwardly biased stop members formed in said sharps protector in diametrically opposed relation to one another, each of said stop members being cut out from said sharps protector along a parting line at a trailing end and opposite sides of each said stop means;
   each trailing end of each stop member extending into an associated accommodation slot when said sharps protector biasing spring is under load and said sharps protector is in its retracted position.

14. The automatic injector of claim 13, further comprising:
   a second catch formed in said reduced diameter section of said cartridge holder sleeve;
   said second catch including a pair of second catch members disposed in diametric opposition to one another;
   each of said second catch members being disposed in leading relation to an associated accommodation slot;
   said trailing end of each stop member extending into an associated second catch member when said sharps protector biasing spring is unloaded and said sharps protector is in its deployed position, thereby preventing displacement of said sharps protector in a leading-to-trailing direction.

15. The automatic injector of claim 14, further comprising:
   first and second guide slots formed in said reduced diameter section of said cartridge holder sleeve in diametrically opposed relation to one another;
   first and second detents formed in a trailing end of said sharps protector in diametrically opposed relation to one another;
   said first and second detents being slideably received within said first and second guide slots, respectively, when said sharps protector is slideably attached to said cartridge holder sleeve;
   said first and second detents abutting a trailing edge of said first and second guide slots, respectively, when said sharps protector is in a retracted position; and
   said first and second detents abutting a leading edge of said first and second guide slots, respectively, when said sharps protector in an extended position.

16. The automatic injector of claim 15, further comprising:
   a ramp formed in said cartridge holder sleeve, said ramps extending from said tapered section in leading relation to said second diameter-reducing shoulder to said reduced diameter section of said cartridge holder sleeve on the trailing side of said second diameter-reducing shoulder;
   said ramp facilitating assembly of said automatic injector;
   said radially inwardly biased stop member slideably engaging said ramp when said sharps protector is secure to said reduced diameter section of said cartridge holder sleeve.

17. The automatic injector of claim 1, further comprising:
   a first diameter-reducing shoulder formed in said cartridge sleeve holder;
   said cartridge sleeve holder having a reduced diameter part in leading relation to said first diameter-reducing shoulder; and
   an externally mounted sharps protector biasing spring under compression having a trailing end disposed in abutting relation to said first diameter-reducing shoulder and a leading end disposed in abutting relation to a trailing end of said sharps protector.

18. The automatic injector of claim 17, further comprising:
   a first catch formed in said reduced diameter section of said cartridge holder sleeve;
   a latch formed in a railing end of said sharps protector, said latch disposed in releasable engagement with said catch when said sharps protector is in its retracted position;
   said latch adapted to be unlatched when said piston biasing means unloads and drives said cartridge in a trailing-to-leading direction;
   whereby unlatching of said latch releases said latch from said catch so that said externally mounted sharps protector biasing means unloads and displaces said sharps protector from said retracted position to said extended position.

19. The automatic injector of claim 18, wherein said first catch includes a pair of catch members formed in said reduced diameter section of said cartridge holder sleeve in diametric opposition to one another and wherein said latch includes a pair of latch members formed in said sharps protector in diametric opposition to one another.

20. The automatic injector of claim 19, further comprising:
   a pair of accommodation slots formed in said reduced diameter section of said cartridge holder sleeve, said accommodation slots being diametrically opposed with respect to one another and each accommodation slot being disposed in spaced apart, leading relation to an associated first catch member;
   a pair of radially inwardly biased stop members formed in said sharps protector in diametrically opposed relation to one another, each of said stop members being cut out from said sharps protector along a parting line at a trailing end and opposite sides of each of said stop members;
   each trailing end of each stop member extending into an associated accommodation slot when said sharps protector biasing spring is under load and said sharps protector is in its retracted position.

21. The automatic injector of claim 18, further comprising:
   a second catch formed in said reduced diameter section of said cartridge holder sleeve;
   said second catch means including a pair of second catch members disposed in diametric opposition to one another;
   each of said second catch members being disposed in leading relation to an associated accommodation slot;
   said trailing end of each stop means extending into an associated second catch member when said sharps protector biasing means is unloaded and said sharps protector is in its deployed position, thereby preventing displacement of said sharps protector in a leading-to-tailing direction.

22. The automatic injector of claim 21, further comprising:
   first and second guide slots formed in said reduced diameter section of said cartridge holder sleeve in diametrically opposed relation to one another;
   first and second detents formed in a trailing end of said sharps protector in diametrically opposed relation to one another;
   said first and second detents being slideably received within said first and second guide slots, respectively, when said sharps protector is slideably attached to said reduced diameter section of said cartridge holder sleeve;
   said first and second detents abutting a trailing edge of said first and second guide slots, respectively, when said sharps protector is in a retracted position; and
   said first and second detents abutting a leading edge of said first and second guide slots, respectively, when said sharps protector is in an extended position.

23. The automatic injector of claim 22, further comprising:
   a ramp formed in said cartridge holder sleeve, said ramp extending from said tapered section to said reduced diameter section of said cartridge holder sleeve;
   said ramp facilitating assembly of said automatic injector;
   said radially inwardly biased stop member slideably engaging said ramp when said sharps protector is secured to said reduced diameter section of said cartridge holder sleeve.

24. The automatic injector of claim 17, further comprising:
   an outer gun sleeve having a first truncate section having a first diameter and a second elongate section having a second diameter greater than said first diameter; and
   said second elongate section of said outer gun sleeve having a leading end positioned in at least partially ensleeving relation to said externally-mounted sharps protector biasing spring.

25. The automatic injector of claim 24, further comprising:
   a clearance space disposed between said leading end of said first truncate section of said outer gun sleeve and a trailing end of said cartridge holder sleeve to enable trailing-to-leading displacement of said outer gun sleeve;
   a safety cap member that slideably receives said first section of said outer gun sleeve;
   said second elongate section of said outer gun sleeve disposed in ensleeving relation to said cartridge holder sleeve;
   said cartridge holder sleeve having a radially-outwardly extending detent formed therein near a leading end thereof;
   a recess formed in said outer gun sleeve for accommodating said radially-outwardly extending detent;
   said recess formed in said outer gun sleeve having a longitudinal extent substantially equal to a longitudinal extent of said radially-outwardly extending detent and said longitudinal extent of said clearance space so that the radially-outwardly extending detent is positioned at a leading end of said recess when said piston biasing means is under compression and said radially-outwardly extending detent is positioned at a trailing end of said recess when said piston biasing is not under compression.

26. The automatic injector of claim 17, further comprising:
   an outer gun sleeve having a first truncate section having a first diameter and a second elongate section having a second diameter greater than said first diameter; and
   said second elongate section of said outer gun sleeve having a leading end positioned in spaced relation to a wailing end of said externally-mounted sharps protector biasing spring in trailing relation thereto so that a pre-firing visual inspection of said liquid medicament is accomplished without looking through said elongate section of said outer gun sleeve.

27. The automatic injector of claim 26, further comprising:
   a clearance space disposed between said leading end of said first truncate section of said outer gun sleeve and a trailing end of said cartridge holder sleeve to enable trailing-to-leading displacement of said outer gun sleeve;
   a safety cap member that slideably receives said first section of said outer gun sleeve;
   said second elongate section of said outer gun sleeve disposed in ensleeving relation to said cartridge holder sleeve;
   said cartridge holder sleeve having a radially-outwardly extending detent formed therein near a leading end thereof;
   a recess formed in said outer gun sleeve for accommodating said radially-outwardly extending detent;
   said recess formed in said outer gun sleeve having a longitudinal extent substantially equal to a longitudinal extent of said radially-outwardly extending detent and said longitudinal extent of said clearance space so that the radially-outwardly extending detent is positioned at a leading end of said recess when said piston biasing spring is under compression and said radially-outwardly extending detent is positioned at a trailing end of said recess when said piston biasing spring is not under compression.

28. An automatic injector, comprising:
   a cartridge holder sleeve having a leading end and an open trailing end;
   said leading end having a diameter that does not exceed a diameter of said cartridge holder sleeve;
   said cartridge holder sleeve having a lumen;
   a cartridge adapted to hold a liquid medicament;
   a cannula hub mounted to a leading end of said cartridge;
   a cannula mounted to a leading end of said cannula hub;
   a piston disposed in trailing relation to said cartridge;
   a spacer disposed in trailing and engaging relation to said piston;
   a spring holder disposed in trailing and engaging relation to said spacer;
   said cartridge, piston, and spring holder being slideably received within said lumen;
   an inner gun sleeve having a leading end positioned within said lumen, said inner gun sleeve secured to said cartridge holder sleeve at said open trailing end of said cartridge sleeve;
   a piston biasing spring under compression having a leading end disposed in abutting relation to said spring holder and a trailing end disposed in abutting relation to a trailing end of said inner gun sleeve;

said trailing end of said inner gun sleeve adapted to releasably engage a trailing end of said spring holder;

said cartridge, piston, spring holder, and cannula being positioned within said lumen in a retracted position when said piston biasing spring is under compression;

said cartridge, piston, and spring holder being positioned within said lumen in an extended position and said cannula extending out of said lumen in leading elation to said cartridge sleeve holder when said piston biasing spring is in repose; and manually operated releasing means for disengaging said trailing end of said spring holder from said trailing end of said inner gun sleeve so that said piston biasing spring unloads when said releasing means is activated;

said manually operated releasing means including manual displacement of said inner gun sleeve in a trailing-to-leading direction;

a sharps protector movably mounted to said leading end of said cartridge holder sleeve and having a retracted position and an extended position;

said sharps protector being in said retracted position when said cannula of said automatic injector is in a retracted position;

said sharps protector being in said extended position when said cannula is in an extended position;

said sharps protector when in said retracted position having a length sufficient to extend beyond a distal end of said cannula when said cannula is in said retracted position; and said sharps protector when in said extended position having a length sufficient to extend beyond a distal end of said cannula when said cannula is in said extended position.

* * * * *